United States Patent [19]

Hoerenz

[11] Patent Number: 4,478,499

[45] Date of Patent: Oct. 23, 1984

[54] OPERATION MICROSCOPE WITH FIXATION DEVICE

[75] Inventor: Peter G. Hoerenz, Hartsdale, N.Y.

[73] Assignee: Carl-Zeiss-Stiftung, Heidenheim/Brenz, Oberkochen, Fed. Rep. of Germany

[21] Appl. No.: 307,207

[22] Filed: Sep. 30, 1981

[51] Int. Cl.³ .............................................. A61B 3/10
[52] U.S. Cl. .................................... 351/211; 351/221
[58] Field of Search ............... 351/205, 219, 221, 206, 351/211; 350/520

[56] References Cited

U.S. PATENT DOCUMENTS

| | | | |
|---|---|---|---|
| 4,195,903 | 4/1980 | Kawase et al. | 350/520 |
| 4,279,478 | 7/1981 | Matsumura | 351/206 |
| 4,283,124 | 8/1981 | Matsumura | 351/206 |
| 4,307,944 | 12/1981 | Schirmer | 351/205 |

Primary Examiner—John K. Corbin
Assistant Examiner—P. M. Dzierzynski
Attorney, Agent, or Firm—Hopgood, Calimafde, Kalil, Blaustein & Judlowe

[57] ABSTRACT

The invention contemplates an operation microscope which incorporates an eye-fixation feature to enable a patient's eye (under microscope observation) to precisely maintain infinity focus and viewing alignment, either with the central axis of the microscope or at desired controllable offset therefrom. Embodiments are shown for incorporation of this feature both as part of the field-illumination optical system associated with the microscope, and otherwise, but nevertheless also utilizing part of the observational optical system of the microscope.

14 Claims, 4 Drawing Figures

OPERATION MICROSCOPE WITH FIXATION DEVICE

BACKGROUND OF THE INVENTION

The present invention refers to an operation microscope, particularly for ophthalmological microsurgery.

It is necessary in certain processes in ophthalmological microsurgery for the patient to bring the visual axis of his eye as closely as possible into the direction of observation (instrument central axis) of the operation microscope and to hold it there for a relatively long time.

So-called fixation objects and fixation lights upon which the patient fixes to thereby bring the visual axis of his eye into a given direction are known in ophthalmological examination instruments. Generally, these aids are arranged at a slight distance from the eye of the patient so that, for persons with poor vision or for older persons, fixation is possible only poorly if at all, even for a short time.

In fundus cameras, a fixation object is known which is arranged in the illumination-ray path in a plane which is imaged onto the retina of the patient, whereby the above-indicated difficulties in fixation are avoided. This fixation object consists of an opaque circular disk of small diameter which can be moved by the doctor in the plane indicated and which makes it possible for him, upon fixation by the patient, to direct the visual axis of the eye of the patient in any desired direction.

As far as I am aware, fixation devices are not known in operation microscopes.

BRIEF STATEMENT OF THE INVENTION

The object of the present invention is to develop an operation microscope such that it becomes possible even for an older person or for a person with defective vision to direct the visual axis of his eye precisely in the direction of observation of the operation microscope and to keep it there, reliably, for a relatively long period of time.

The invention achieves this object in a fixation device for aligning the visual axis of the eye of the patient, by providing the device with a fixation mark and an objective to focus the mark at infinity, substantially in the direction of microscope observation. The microscope incorporating the invention may illustratively be, but is not necessarily, a binocular stereo microscope, having a single main objective which serves both observation-ray paths of the stereo system.

In one advantageous embodiment, a separate ray path is used for the fixation device. The separate ray path may be precisely coaxial with the instrument axis and, in the case of a binocular stereo microscope, may use the single main objective which serves both observation-ray paths of the stereo system, the fixation-ray path exiting from the instrument between the two observation-ray paths thereof. However, such precise symmetry is not necessary, since slight deviations can be compensated by displacing the fixation mark transverse to the ray path. In a second embodiment, the fixation-ray path is deflected via a beam splitter into one of the two stereo observation-ray paths.

To compensate for the effect of the main operation-microscope objective on the ray path for the fixation mark and to correct for any possible defect in vision of the patient, one or more lenses are advisedly arranged swingably in front of the main objective. A turret mount is particularly advantageous for this purpose.

In another embodiment, the fixation mark is brought into that plane of a coaxial or approximately coaxial illumination-ray path which is focused at infinity. In this case, only a limited correction for the defective vision of the patient can be effected with the lens turret described above, since this correction also affects the illumination-ray path. It is therefore particularly advantageous to effect the correction solely, or at least additionally, by displacement of the fixation mark in the direction of the optical axis, whereby the illumination-ray path is not affected.

Other embodiments of the invention are described.

DETAILED DESCRIPTION

The invention will be described in further detail in conjunction with the accompanying drawings, in which.

Figure 1:
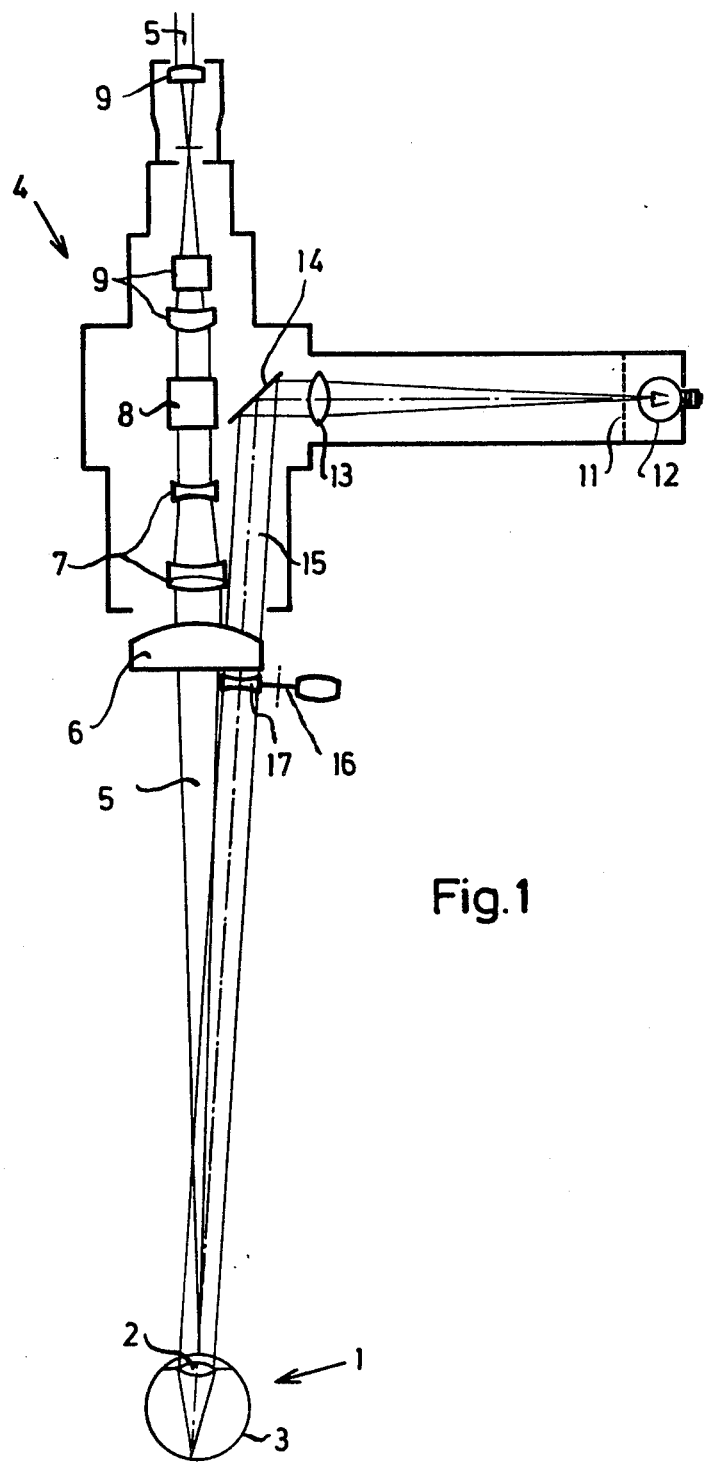
FIG. 1 is an optical diagram of a binocular stereo operation microscope with a fixation device in which the ray path for the fixation mark is arranged independently of the two observation-ray paths of the microscope.

In FIG. 1, 1 designates the eye of the patient, 2 the lens of the eye, and 3 the retina. An operation microscope 4 has two observation-ray paths which lie in front of and behind the plane of the drawing, and only one (5) of these ray paths is shown. A main objective 6 enables focus of both observation-ray paths upon the exterior surface of eye 1. Behind a magnification changer 7, a splitter cube 8 is arranged in each beam path; such cubes are customarily used for auxiliary access to the observation-ray paths, as for documentation or co-worker equipment. Finally, one of the two eyepieces is shown at 9.

A fixation device of the invention consists of a fixation mark 11, which is illuminated by a lamp 12 and focused at infinity by an objective 13. An element 14 directs the fixation-ray path 15 through the main objective 6 and onto the eye 1 of the patient. In order to compensate for the optical effect of the main objective 6, a swingable compensating lens 17 is arranged in the fixation-ray path 15 so that collimated light (i.e., a parallel bundle of light) strikes the eye 1, and an image of the fixation mark 11 is produced on the retina 3 by the eye lens 2, being thereby accommodated to infinity.

For patients with defective vision, lenses of different refractive power can be brought into the ray path in place of the compensating lens 17. This is advisedly done by means of a rotatable turret 16. It will be understood that in the event of using a turret as at 16, its selectively available lenses may be designed to cooperate solely with the main objective 6 to project collimated light in the fixation-ray path to eye lens 2, thus eliminating lens 13 and enabling the fixation mark 11 and its illumination 12 to be arranged closer to the observation-ray path.

It will also be understood that the fixation-ray path 15 can be arranged precisely in the instrument axis of the operation microscope and therefore between the two observation-ray paths. However, this is not necessary to achieve the object of the invention. In the case shown in FIG. 1, the fixation mark 11 need merely be so positioned in a plane perpendicular to the observation-ray paths that the center of its image strikes the retina exactly on the observation axis, i.e. on the central axis of the instrument; however, to achieve such centering of the image of the fixation mark at the retina, it will be appreciated that the fixation-ray path 15 need not necessarily pass through the main objective 6.

Figure 2:
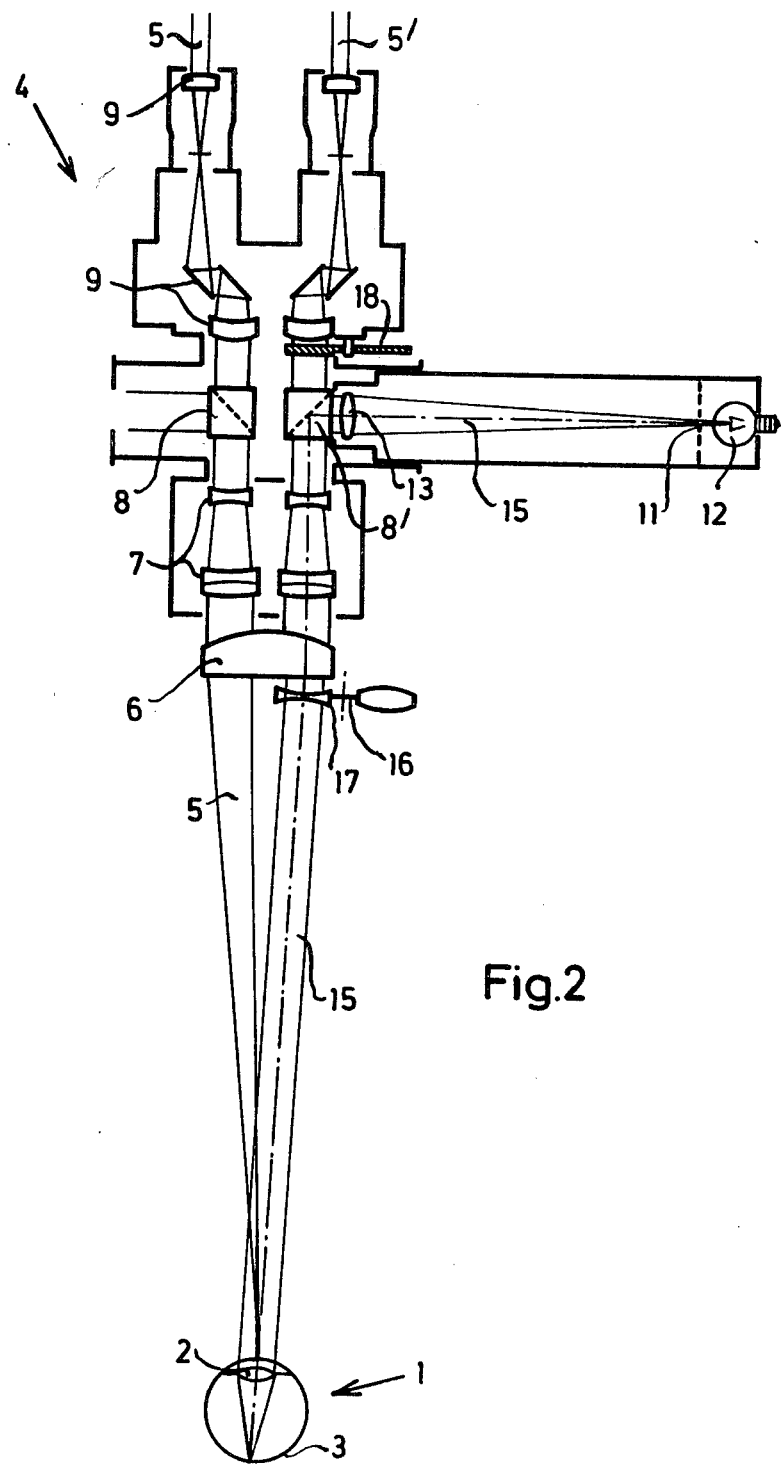
FIG. 2 is a similar diagram, viewed normal to the plane defined by the two microscope observation-ray paths, to show another embodiment in which the ray path for the fixation mark is conducted through one of the two observation-ray paths.

In FIG. 2, as distinguished from FIG. 1, an operation microscope is shown with both of its observation-ray paths 5—5' in the plane of the drawing, i.e., viewed 90° from the aspect of FIG. 1. In the embodiment of FIG. 2, the fixation-ray path 15, together with a fixation mark 11 focused at infinity by an objective 13, is deflected by a beam splitter 8' into one (5') of the two observation-ray paths, and the correction lens 17 (needed for the target 11 to be observed by the patient) defocuses the doctor's observation on path 5'. The latter path therefore may not be available to the doctor for the time during which the patient directs the visual axis of his eye on the fixation mark 11. And if the doctor chooses to rely on monocular observation via path 5, without disturbance from the patient's use of path 5' to view the fixation mark 11, the observational use of path 5' can be selectively interrupted by a swingable beam shutter 18.

It will be understood that in the embodiments of both FIG. 1 and FIG. 2, the fixation mark 11 can alternatively be illuminated via a light guide or that it can also be self-illuminating. Further, the fixation mark 11 can be developed as a cross, circle or any other customary form.

Figure 3:
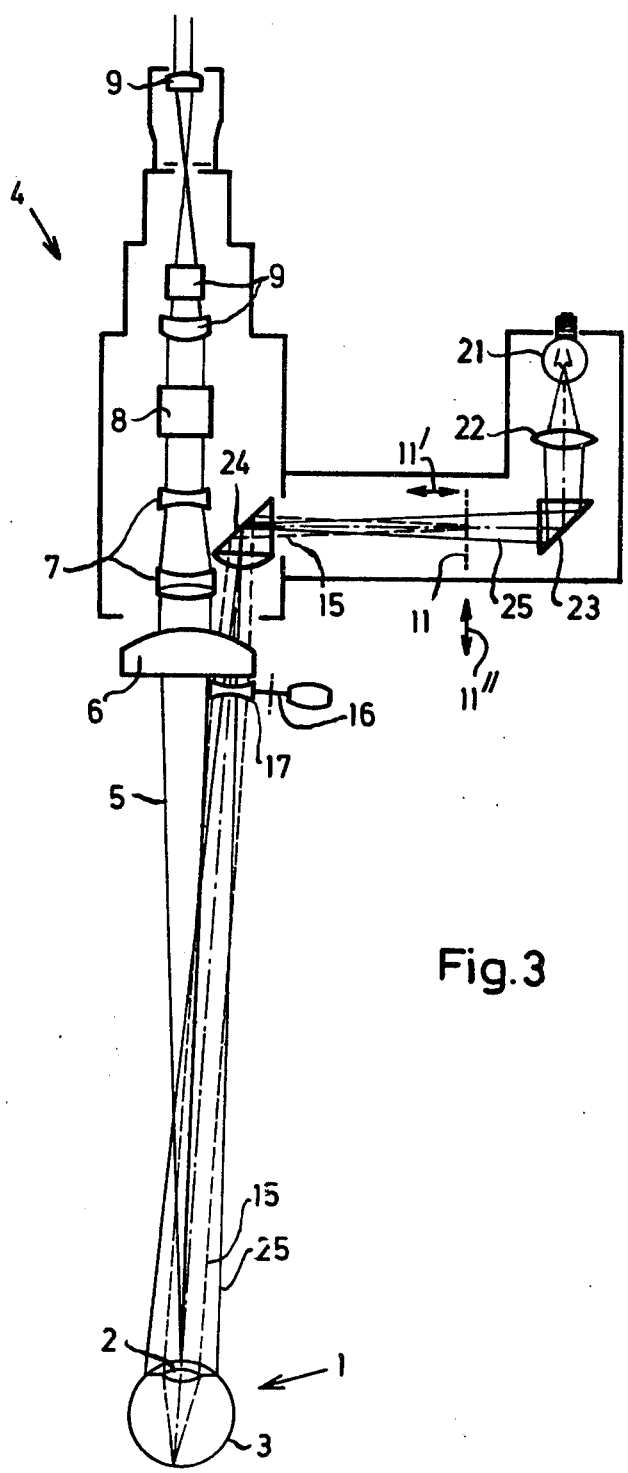
FIG. 3 is a diagram viewed as in FIG. 1, to show a further embodiment in which the fixation mark is arranged in an illumination-ray path.

In the embodiment of FIG. 3, an approximately coaxial illumination-ray path is designated 25, the same providing illumination of the observation field. Projection on path 25 involves an incandescent bulb 21 whose filament is focused, by a condenser 22 and via a deflection prism 23, at the deflection surface of a prism 24. The deflection prism 24 is positioned close to the stereo observation-ray paths, so that illumination with the ray path 25 takes place practically coaxially. The deflection-prism (24) surface facing the main objective 6 is developed as a lens which, coactive with the main objective 6, focuses the plane of condenser 22 in the plane of eye lens 2. The fixation mark 11 is so arranged on ray path 15 between prisms 23 and 24 that mark 11 is focused at infinity by the deflection-prism (24) lens (coacting with the main objective 6), and so that an image of the fixation mark 11 is formed by the eye lens 2 on the retina 3.

For eyes with defective vision, a turret 16 with correction lenses 17 can be arranged behind the main objective 6, in the same way as in the other embodiments. The correction range is, however, limited in this case by the fact that the lenses also act on the illumination-ray path 25. It is therefore better to effect the correction by displacing the fixation mark 11 in the direction of the optical axis, which has no effect on the illumination-ray path 25; a double-headed arrow 11' will be understood to schematically indicate means for such selective displacement of mark 11. Of course, if desired, both possibilities of correction can be concurrently used.

The fixation mark 11 for the FIG. 3 embodiment may illustratively be an opaque disk of small diameter or a colored transparent mark on a glass disk. Alternatively, mark 11 may comprise a small circle of greater brightness, produced as by a filter having greater light-transmittance at its center than on the rest of its surface.

Figure 4:
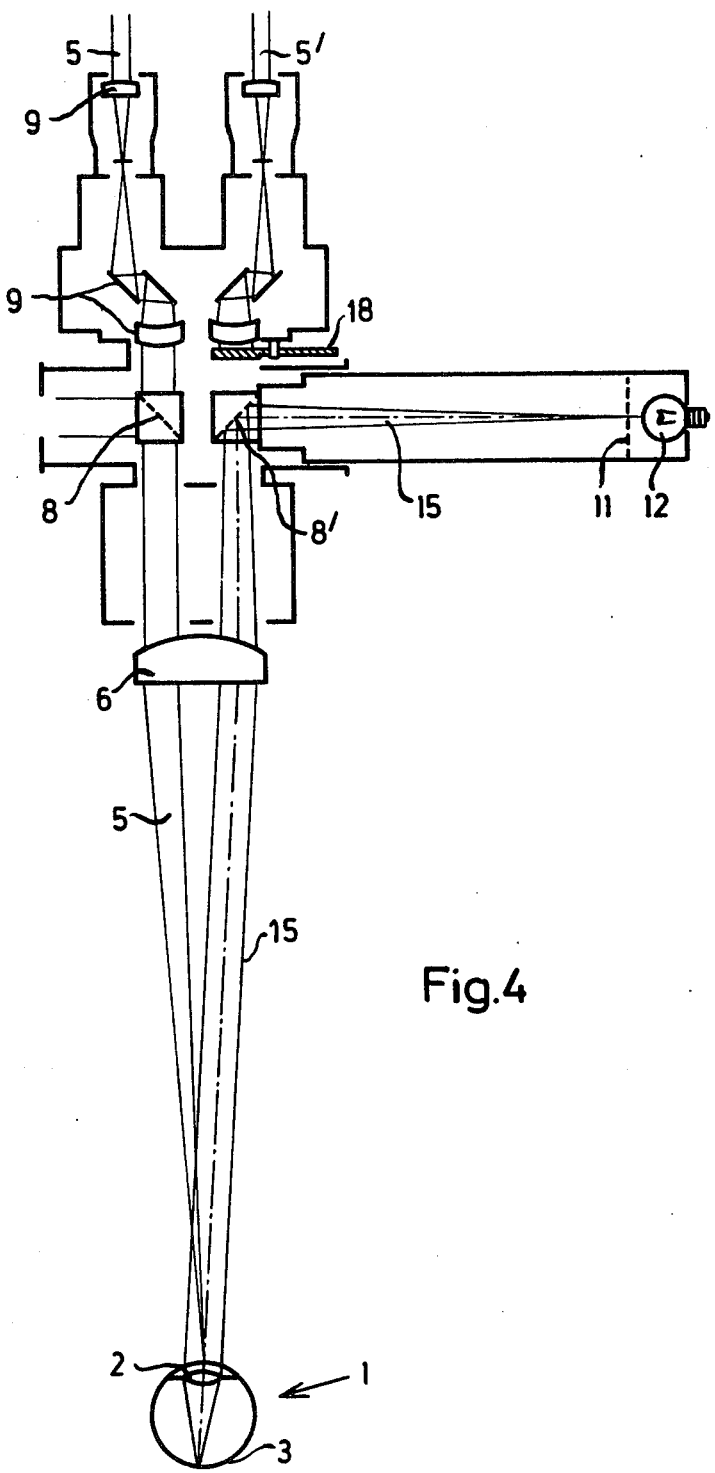
FIG. 4 is a diagram viewed as in FIG. 2, to show a modification of FIG. 2.

In the arrangement of FIG. 4, the complexity of FIG. 2 is reduced in a beam-splitting imposition of the fixation-ray path 15 on the observation-ray path 5'. The principal simplifying point of difference lies in the use of the main objective 6 alone as the means of imaging the fixation mark 11 on the retina 3, by positioning the mark 11 at the focal point of objective 6. It will be understood that use of the expression "beam splitter" in connection with element 8' in FIG. 4 is not intended to prescribe a 50:50 splitting of light intensity, but rather that the amount of reflected light passing via the mark-projection system 15 may be scaled to much less than 50 percent of the total light transmittance shared by the observation path 5' and by the mark-projection path 15; for example, the light reflected by element 8' along path 15 may be as little as 10 percent of a perfect (or total) reflection. This being the case, the surgeon may choose to tolerate internal reflection of mark-projecting light, because the low level of its reflection into the path 5' does not spoil his depth perception via the focused stereo system; but if he chooses to avoid even this much reflection and to rely on monocular observation via path 5 alone, then shutter 18 is at his disposal for the purpose. What has been said as to less-than-50 percent reflection at 8' will be understood to apply to use of a small 45° mirror at 8', wherein mirror area is a small fraction of the full effective area of the observation-ray bundle in path 5'.

In all embodiments, it is advantageous not merely to make the fixation mark adjustable, as at 11' but also to make it selectively displaceable in a plane locally perpendicular to the fixation-ray path, as indicated by a double-headed arrow 11" in FIG. 3. Transverse adjustment, as by means 11", will be seen to enable the doctor to selectively direct the visual axis of the patient's eye 1 to desired offset from the instrument axis; and notched or detent action identified with one or more standardized offset adjustments of means 11", which may be two-component adjustments, will be understood to assure quick and precise shifting between standardized offsets.

What is claimed is:

1. In a binocular stereo operation microscope wherein a single main objective serves each of two spaced optical systems and has the capability of focusing said optical systems at the exterior surface of the eye of a patient under observation, the improvement in which a fixation-mark and light-projection system therefor also utilizes said main objective in its optical path of fixation-mark projection, whereby the main objective is part of the light-projection system, said light-projection system projecting collimated light upon the patient's eye so that the patient's eye can see the mark at infinity through the same objective as is being used by an examining physician to observe exterior surface of the patient's eye.

2. The improvement of claim 1, in which the fixation-mark projection system includes a light-reflecting element between the two spaced optical systems of the binocular microscope.

3. The improvement of claim 1, in which the fixation-mark projection system includes a light-reflecting element on one of the two spaced optical systems of the binocular microscope.

4. The improvement of claim 1, in which said main objective is the only focusing element serving said fixation-mark projection system.

5. The improvement of claim 1, wherein the microscope includes a beam splitter in one of the two spaced optical systems, and wherein the optical path of fixation-mark projection is deflected by said beam splitter into said one of the two spaced optical systems.

6. The improvement of claim 5, wherein a selectively operable beam shutter is positioned in front of the beam splitter.

7. The improvement of claim 1, wherein a corrective lens is selectively positionable in the optical path of fixation-mark projection and at a location independent of the two spaced optical systems of said main objective.

8. The improvement of claim 7, wherein said corrective lens is one of a plurality of lenses of different refractive power, turret-mounted for selective positioning in the optical path of fixation-mark projection.

9. The improvement of claim 1, wherein in the optical path of fixation-mark projection, said main objective focuses the fixation mark at infinity.

10. The improvement of claim 1, wherein the optical path of fixation-mark projection is illuminated by an incandescent lamp.

11. The improvement of claim 1, wherein the fixation mark is self-illuminating.

12. The improvement of claim 1, wherein the fixation mark is arranged in the optical path of a substantially coaxial illuminating device.

13. The improvement of claim 1, wherein the fixation mark is displaceable in the direction of the optical path of fixation-mark projection.

14. The improvement of claim 1, wherein the fixation mark is laterally displaceable in a plane locally perpendicular to the optical path of fixation-mark projection.

* * * * *